(12) United States Patent
Houben

(10) Patent No.: US 7,069,078 B2
(45) Date of Patent: Jun. 27, 2006

(54) INSULIN-MEDIATED GLUCOSE UPTAKE MONITOR

(75) Inventor: Richard Houben, Lanaken (BE)

(73) Assignee: Medtronic, Inc., Minneapolis, MN (US)

(*) Notice: Subject to any disclaimer, the term of this patent is extended or adjusted under 35 U.S.C. 154(b) by 412 days.

(21) Appl. No.: 10/127,033

(22) Filed: Apr. 22, 2002

(65) Prior Publication Data
US 2003/0199925 A1    Oct. 23, 2003

(51) Int. Cl.
*A61N 1/365* (2006.01)

(52) U.S. Cl. ............................................. 607/18; 607/9
(58) Field of Classification Search ......... 600/513.517; 607/3–6, 9, 22, 25
See application file for complete search history.

(56) References Cited

U.S. PATENT DOCUMENTS

| 4,146,029 A | * | 3/1979 | Ellinwood, Jr. | 604/891.1 |
| 5,660,163 A | | 8/1997 | Schulman et al. | 600/345 |
| 5,730,125 A | * | 3/1998 | Prutchi et al. | 600/323 |
| 5,741,211 A | | 4/1998 | Renivre et al. | 600/300 |
| 5,999,848 A | | 12/1999 | Gord et al. | 607/2 |
| 6,081,736 A | | 6/2000 | Colvin et al. | 600/377 |
| 6,119,028 A | | 9/2000 | Schulman et al. | 600/345 |
| 6,175,752 B1 | | 1/2001 | Say et al. | 600/345 |
| 6,212,416 B1 | | 4/2001 | Ward et al. | 600/345 |
| 6,221,011 B1 | | 4/2001 | Bardy | 600/300 |
| 6,259,937 B1 | | 7/2001 | Schulman et al. | 600/345 |
| 6,277,072 B1 | | 8/2001 | Bardy | 600/300 |
| 6,360,888 B1 | | 3/2002 | McIvor et al. | 206/305 |

FOREIGN PATENT DOCUMENTS

WO    0191854    6/2001

OTHER PUBLICATIONS

International Search Report for International No. PCT/US03/12145 dated Aug. 26, 2003.
United States Patent Application Publication No. US 2002/0026141 A1 published Feb. 28, 2002.

* cited by examiner

*Primary Examiner*—Carl Layno
(74) *Attorney, Agent, or Firm*—Medtronic, Inc.

(57) ABSTRACT

An implanted medical device may detect the onset of impaired glucose tolerance or Type II diabetes. The implanted medical device may have additional functionality. For example, the implanted medical device may be a pacemaker or a pressure monitor, but may also monitor insulin-mediated glucose uptake by processing electrical signals from the heart. An implanted medical device that monitors insulin-mediated glucose uptake may be implanted in a patient who has not been diagnosed with impaired glucose tolerance or Type II diabetes, and may give the patient early warning if these conditions develop.

22 Claims, 8 Drawing Sheets

INSULIN-MEDIATED GLUCOSE UPTAKE MONITOR

FIELD OF THE INVENTION

The invention relates to patient monitoring systems, and more particularly, to patient monitoring systems that receive an electrical cardiac signal indicative of cardiac activity.

BACKGROUND

Diabetes mellitus is the most common of endocrine disorders, and is characterized by inadequate insulin action. Diabetes mellitus has two principal variants, known as Type I diabetes and Type II diabetes. The latter is also referred to as DM/II (diabetes mellitus type II), adult-onset diabetes, maturity-onset diabetes, or NIDDM (non-insulin dependent diabetes mellitus).

Type II diabetes generally develops in adulthood, and the risk of development of Type II diabetes increases with age. Factors such as obesity also contribute to the risk. A patient suffering from Type II diabetes secretes insulin, but the insulin's target cells are less sensitive to insulin. Symptoms of Type II diabetes are typically slow to appear, and a patient having Type II diabetes may not be aware of his condition. A blood test may show whether the patient has impaired glucose tolerance (IGT), which is often a precursor to Type II diabetes, or compensated Type II diabetes. Unless addressed with treatment such as diet and exercise, these conditions may develop into uncompensated Type II diabetes, a very serious condition.

Patients at risk for diabetes may use a glucose sensor. Most glucose sensors presently in common use are based on electrochemical methods such as the electroenzymatic method where blood glucose is oxidized under glucose-oxidase control, producing gluconic acid and hydrogen peroxide. Alternately, the produced gluconic acid can be determined directly. Both of these sensor types, however, suffer from stability problems. Optical glucose sensors have been tried, but optical sensors may not be feasible for long-term continuous monitoring or for implantable applications.

Poor diet and lack of exercise may not only increase the risk of Type II diabetes, but may increase the risk of heart disease as well. Obesity may, for example, contribute to high blood pressure, which increases the workload of the heart. In addition, the risk of coronary heart disease, like the risk of developing Type II diabetes, increases with age.

In commonly-assigned U.S. Pat. No. 5,741,211 to Renirie, et al., a possible relationship between diabetes mellitus and coronary heart disease was discussed. A correlation between electrocardiogram (ECG) changes and blood glucose was described, and systems and methods were described whereby changes in blood insulin could be monitored as a function of ECG signals. The system applied signal processing to the continuously sensed ECG signals to discriminate selected portions such as the QRS complex and the T-wave. The discriminated portions may be further processed to determine a relationship between the signal and the patient's blood insulin and/or blood glucose levels. The '211 patent is hereby incorporated by reference herein in its entirety.

Long-term monitoring systems and devices known in the art typically involve chemically based sensors. These sensors are typically not medically or economically beneficial for a patient who may be at risk of developing diabetes. Examples of these techniques and/or devices may be found in the issued U.S. Patents listed in Table 1 below.

TABLE 1

| U.S. Pat. No. | Inventor | Issue Date |
|---|---|---|
| 5,660,163 | Schulman et al. | Aug. 26, 1997 |
| 5,999,848 | Gord et al. | Dec. 7, 1999 |
| 6,081,736 | Colvin et al. | Jun. 27, 2000 |
| 6,119,028 | Schulman et al. | Sep. 12, 2000 |
| 6,175,752 B1 | Say et al. | Jan. 16, 2001 |
| 6,212,416 B1 | Ward et al. | Apr. 3, 2001 |
| 6,221,011 B1 | Bardy | Apr. 24, 2001 |
| 6,259,937 B1 | Schulman et al. | Jul. 10, 2001 |
| 6,277,072 B1 | Bardy | Aug. 21, 2001 |
| 6,360,888 B1 | McIvor et al. | Mar. 26, 2002 |

All patents listed in Table 1 above are hereby incorporated by reference herein in their respective entireties. As those of ordinary skill in the art will appreciate readily upon reading the Summary of the Invention, Detailed Description of the Preferred Embodiments and claims set forth below, many of the devices and methods disclosed in the patents of Table 1 may be modified advantageously by using the techniques of the present invention.

SUMMARY OF THE INVENTION

The present invention has certain objects. That is, various embodiments of the present invention provide solutions to one or more problems existing in the prior art with respect to insulin and/or glucose monitors. These problems include, for example, the lack of medical or economic benefit associated with implanting an insulin or glucose monitor in a patient who has not been diagnosed as diabetic. The problems also include a lack of robustness of sensors that may be used to perform the monitoring over an extended period of time. Various embodiments of the present invention have the object of solving at least one of the foregoing problems.

It is an object of the invention to monitor the development of IGT or Type II diabetes in a patient with an implanted medical device. In particular, it is an object of the present invention to monitor insulin-mediated glucose uptake, which may be indicative of IGT or Type II diabetes. Because the patient may not have been diagnosed with IGT or Type II diabetes, surgical implantation of such a device may not be justified medically or economically.

In a patient who receives an implanted medical device that principally performs another function, however, the implanted medical device may also monitor insulin-mediated glucose uptake. An implantable cardiac pacemaker, for example, may have a principal function of monitoring the patient's heart rhythms and delivering appropriate therapy to correct arrhythmias. The same pacemaker may be further configured to monitor insulin-mediated glucose uptake as an additional benefit. The implantation of the pacemaker may be justified medically and economically, and may include an implanted insulin-mediated glucose uptake monitor with no additional surgery or inconvenience to the patient. The patient may receive the benefit of monitoring even when the patient has not have been diagnosed with IGT or diabetes, enabling early detection of such conditions.

It is a further object of the invention to enable implantable medical devices of many types to monitor insulin-mediated glucose uptake. Many implantable devices may be configured to receive an electrical signal from the heart, such as an ECG signal or an electrogram (EGM) signal. Other implantable devices may be adapted to receive an electrical signal from the heart. These devices, which may have other principal functions, may also be applied to monitor insulin-mediated glucose uptake.

It is also an object of the invention to provide an early warning in patients who do develop IGT or Type II diabetes. IGT and Type II diabetes typically develop slowly, and early detection may lead to more effective treatment and fewer complications. These conditions often respond to therapy such as administration of glucose lowering agents, changes in diet and/or exercise. When IGT or diabetes is detected early, a greater array of therapeutic options are available to the patient. It is an additional object of the invention to monitor the effectiveness of the therapy.

An additional object of the invention is to provide a robust system for monitoring insulin-mediated glucose uptake. Because the monitoring may take place over an extended period of time, the implanted components should be able to operate for a long time under a wide variety of conditions. Many glucose sensors are ill-suited to long-term monitoring.

Various embodiments of the invention may possess one or more features capable of fulfilling the above objects. The invention analyzes electrical signals from the heart to assess the patient's insulin-mediated glucose uptake. In an exemplary embodiment, the invention analyzes the electrical signals that follow the ingestion of a meal. The invention further employs electrodes as sensors, which are more robust than chemically based sensors. The electrodes may be coupled to an implantable medical device that performs other principal functions, such as a pacemaker, a pacemaker-cardioverter-defibrillator, a pressure monitor, a nerve stimulator, a muscle stimulator, a drug delivery device, and a cardiac monitor. The invention provides additional functionality to the implantable medical device.

The invention may offer one or more advantages in addition to those mentioned above. Patients needing an implantable medical device may receive blood insulin and/or blood glucose monitoring as an added benefit, without the necessity of a separate, dedicated insulin or glucose monitoring device. The techniques of the invention may help identify the development of conditions that otherwise might not be noticed by the patient, and may provide the patient with an early warning of IGT or Type II diabetes. With early warning, the patient may take steps that can slow, and possibly reverse, the progression of the disease.

The details of one or more embodiments of the invention are set forth in the accompanying drawings and the description below. Other features, objects, and advantages of the invention will be apparent from the description and drawings, and from the claims.

DETAILED DESCRIPTION OF THE PREFERRED EMBODIMENTS

In the following detailed description of the preferred embodiments, reference is made to the accompanying drawings that form a part hereof, and in which are shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
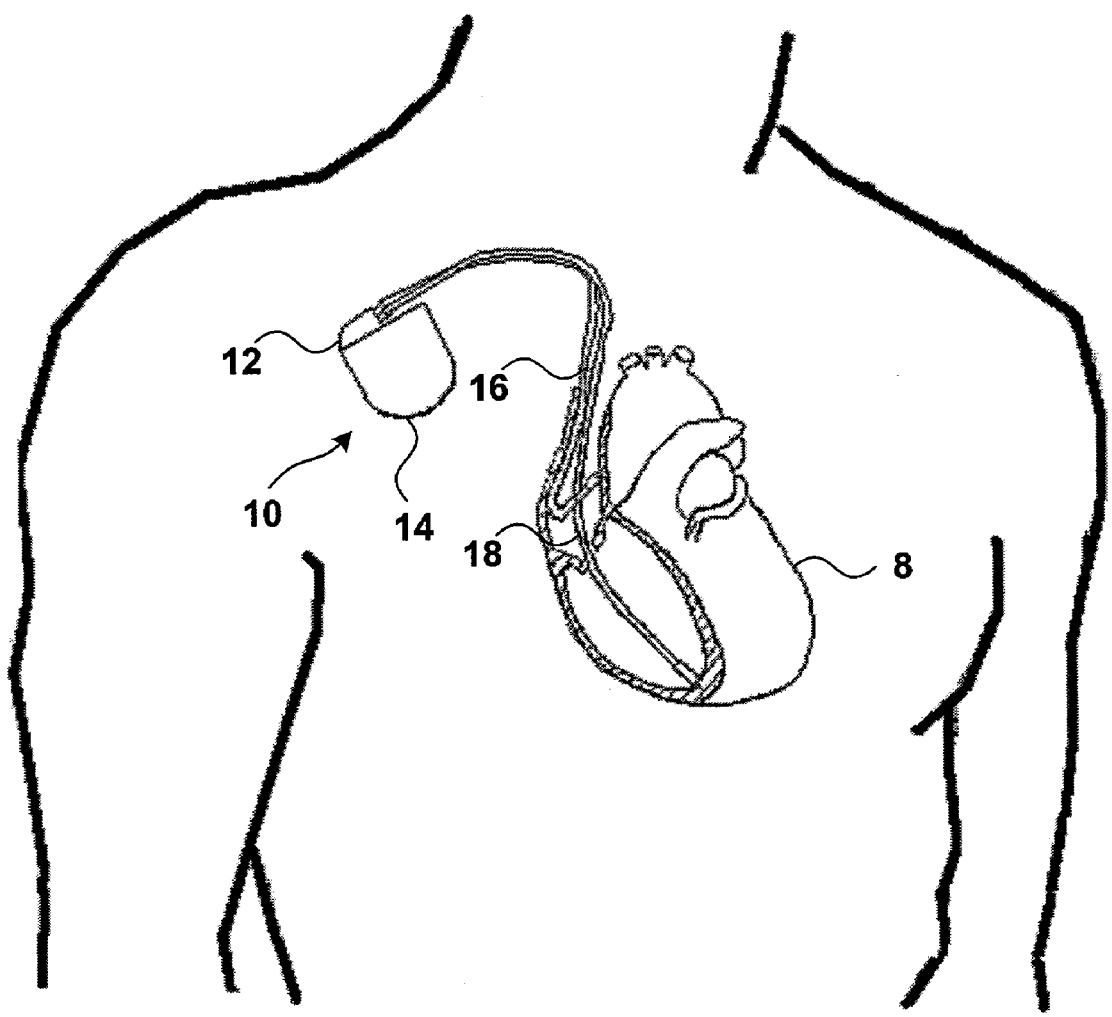
FIG. 1 is a schematic view of an implantable medical device in the chest of a patient.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to connector module 12 of hermetically sealed enclosure 14 and implanted near human or mammalian heart 8. Pacing and sensing leads 16 and 18 sense electrical signals attendant to the depolarization and repolarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al., or U.S. Pat. No. 5,144,949 to Olson, all hereby incorporated by reference herein, each in its respective entirety.

Electrical signals detected via pacing and sensing leads 16 and 18 may be used to monitor blood insulin and/or blood glucose using techniques that will be described below. The invention is not limited to the particular embodiment shown in FIG. 1 or to other exemplary embodiments shown in subsequent figures.

Figure 2:
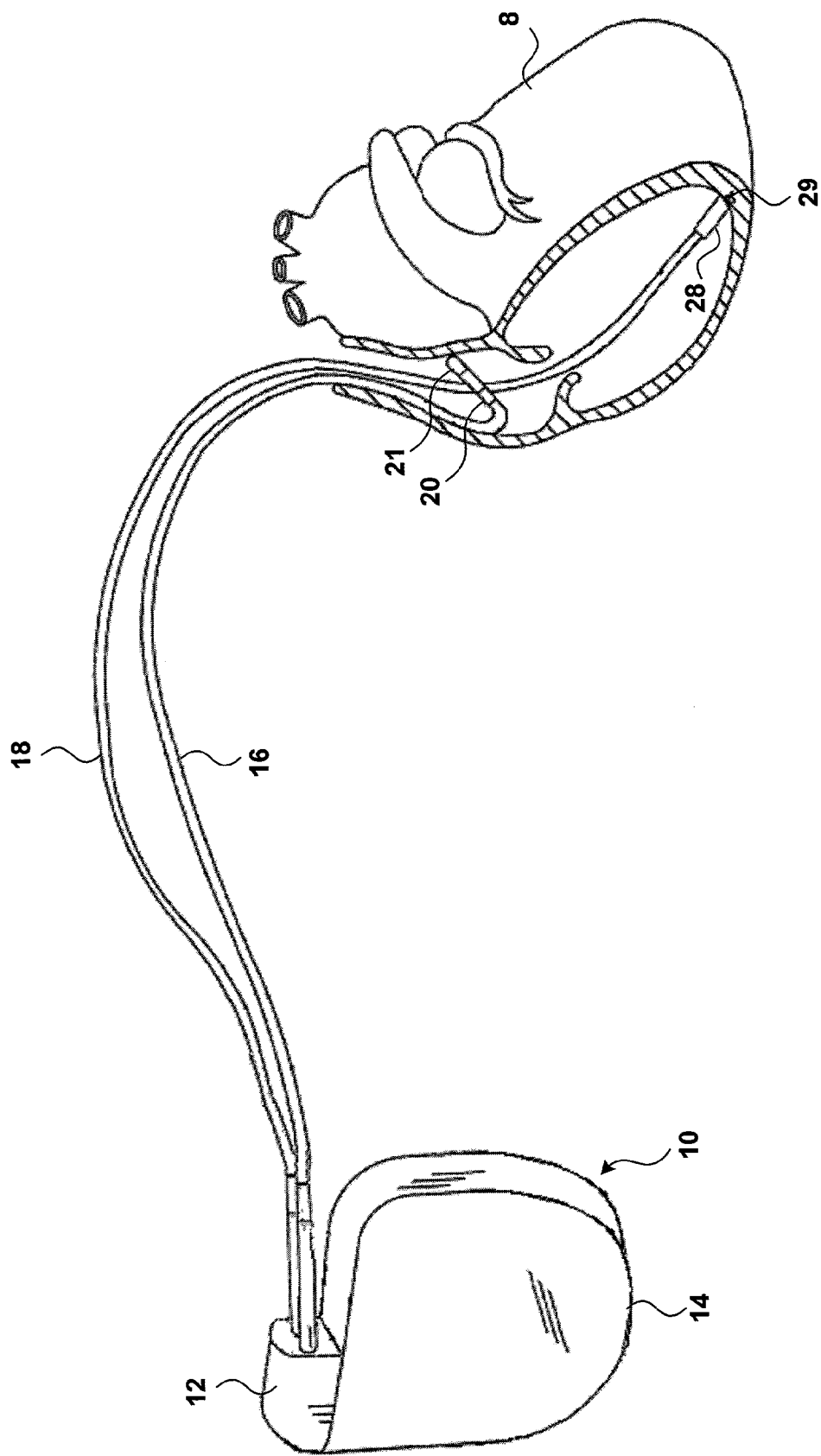
FIG. 2 shows the implantable medical device of FIG. 1 located in and near a heart.

FIG. 2 shows connector module 12 and hermetically sealed enclosure 14 of IMD 10 located in and near human or mammalian heart 8. Atrial and ventricular pacing leads 16 and 18 extend from connector module 12 to the right atrium and ventricle, respectively, of heart 8. Atrial electrodes 20 and 21 disposed at the distal end of atrial pacing lead 16 are located in the right atrium. Ventricular electrodes 28 and 29 disposed at the distal end of ventricular pacing lead 18 are located in the right ventricle.

Figure 3:
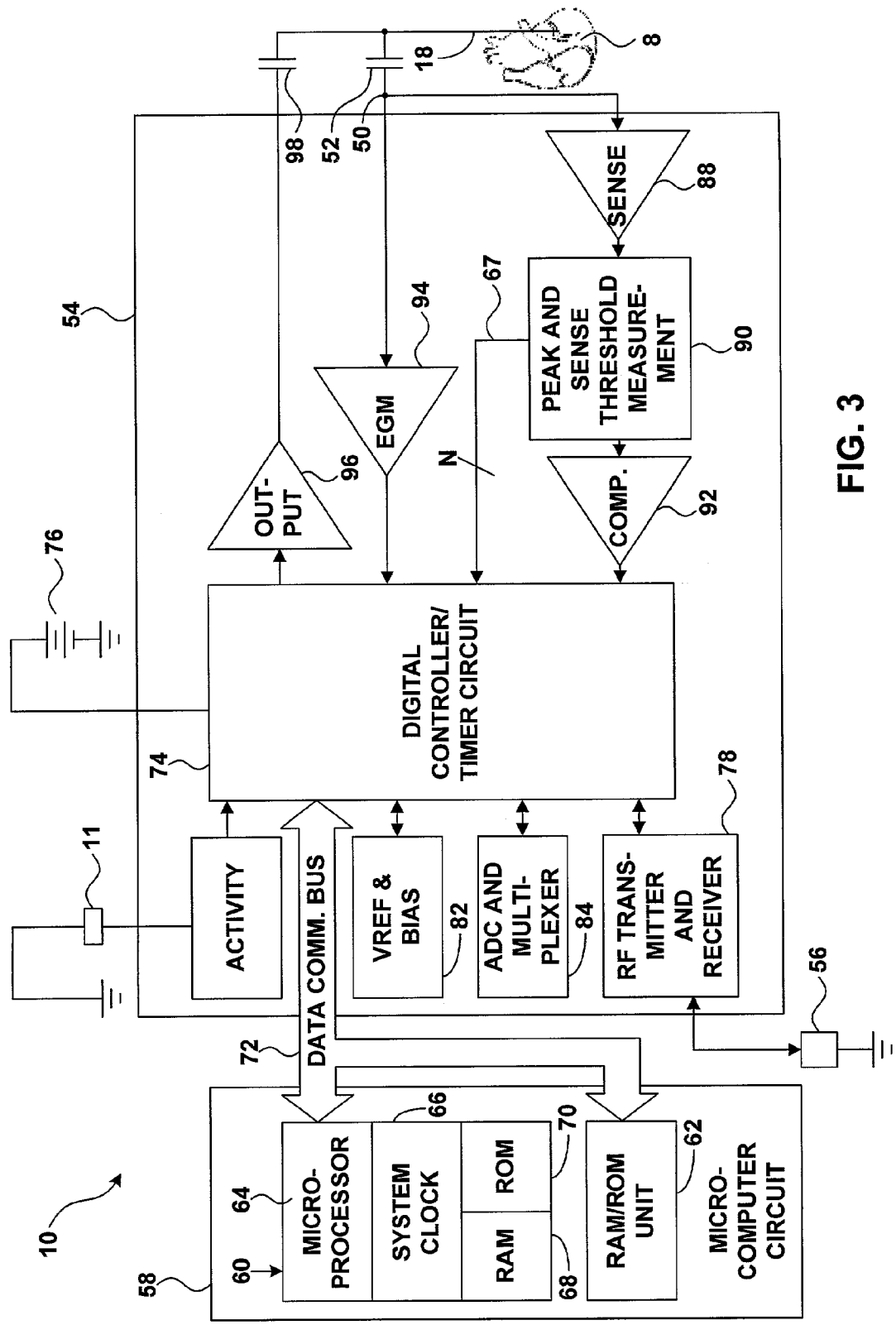
FIG. 3 is a block diagram illustrating the constituent components of an implantable medical device.

FIG. 3 shows a block diagram illustrating the constituent components of IMD 10 in accordance with one embodiment of the present invention, where IMD 10 is a pacemaker having a microprocessor-based architecture. IMD 10 is shown as including activity sensor or accelerometer 11, which is preferably a piezoceramic accelerometer bonded to a hybrid circuit located inside enclosure 14 (shown in FIGS. 1 and 2). Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto. However, it is understood that similar circuitry and connections not explicitly shown in FIG. 3 apply to lead 16 (shown in FIGS. 1 and 2).

IMD 10 in FIG. 3 is most preferably programmable by means of an external programming unit (not shown in the figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing with heart 8, activity sensor 11, antenna 56 and circuits for the application of stimulating pulses to heart 8. The rate of heart 8 is controlled by software-implemented algorithms stored within microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, VREF and bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled from microprocessor 64 via data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is also provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. The electrogram signal may also be useful in monitoring blood insulin and/or blood glucose. Output pulse generator 96 provides amplified pacing stimuli to patient's heart 8 through coupling capacitor 98 in response to a pacing trigger signal provided by digital controller/timer circuit 74 each time either (a) the escape interval times out, (b) an externally transmitted pacing command is received, or (c) in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of sense amplifier 88, output pulse generator 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive modes, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with one or more leads or with multiple-chamber pacemakers, for example. At least some embodiments of the present invention may be applied equally well in the contexts of single-, dual-, triple- or quadruple- chamber pacemakers or other types of IMD's. See, for example, U.S. Pat. No. 5,800,465 to Thompson et al., hereby incorporated by reference herein in its entirety, as are all U.S. Patents referenced therein. IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, and U.S. Pat. No. 4,821,723 to Baker et al., all hereby incorporated by reference herein, each in its respective entirety.

Figure 4:
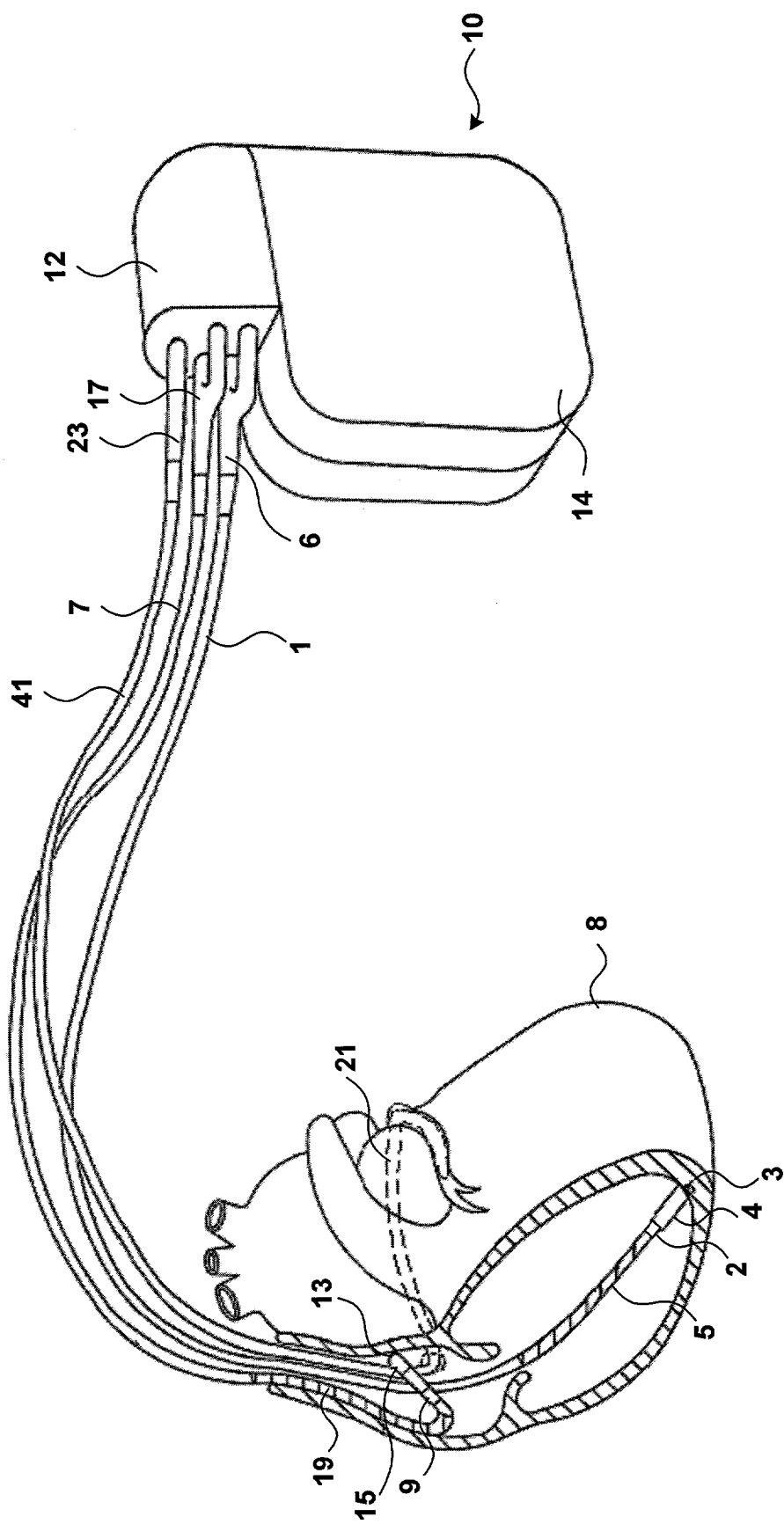
FIG. 4 shows another implantable medical device, a pacemaker-cardioverter-defibrillator, located in and near a heart.
Figure 5:
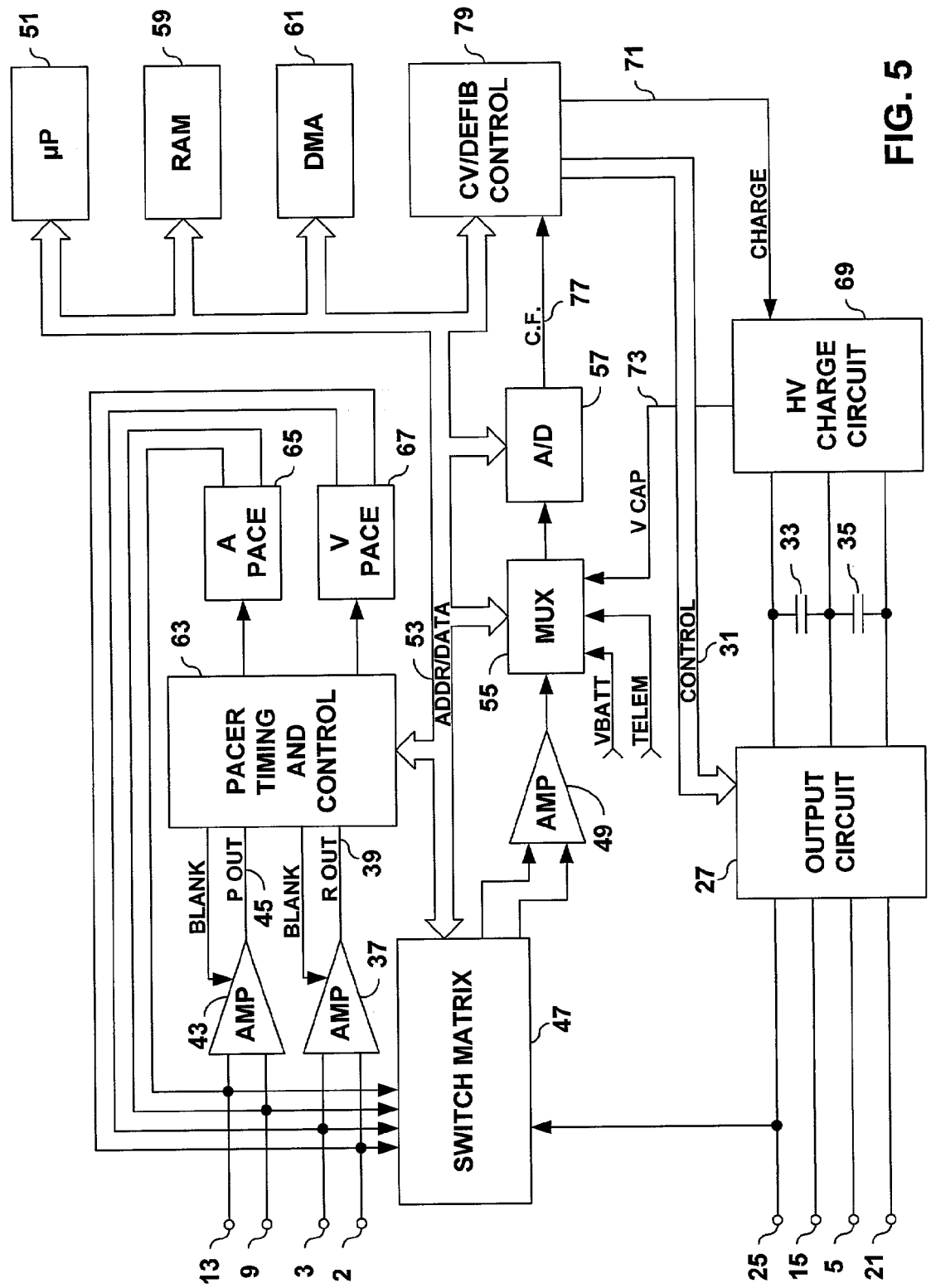
FIG. 5 is a functional schematic diagram of one embodiment of an implantable medical device.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Elongated coil electrode 5, which is a defibrillation electrode 5, may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. Elongated coil defibrillation electrode 41 may be about 5 cm in length.

IMD 10 is shown in FIG. 4 in combination with leads 1, 7 and 41, and lead connector assemblies 23, 17 and 6 inserted into connector module 12. Optionally, insulation of the outward facing portion of housing 14 of IMD 10 maybe provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of IMD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of IMD 10. Electrodes 25, 15, 21 and 5 are coupled to high voltage output circuit 27, which includes high voltage switches controlled by CV/defib control logic 79 via control bus 31. Switches disposed within circuit 27 determine which electrodes are employed and which electrodes are coupled to the positive and negative terminals of a capacitor bank (which includes capacitors 33 and 35) during delivery of defibrillation pulses.

Electrodes 2 and 3 are located on or in the ventricle of the patient and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium of the patient and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824 to Keimel et al., hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single- and dual-chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R—R intervals, P—P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence of sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R—R or P—P intervals of an average rate indicative of tachyarrhythmia or an unbroken series of short R—R or P—P intervals. The rate of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al., and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/8198, by Adams et al., and in the article "Automatic Tachycardia Recognition," by Arzbaecher et al., published in PACE, May-June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al., U.S. Pat. No. 4,880,005, issued to Pless et al., U.S. Pat. No. 4,726,380, issued to Vollmann et al., and U.S. Pat. No. 4,587,970, issued to Holley et al., all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 79, which initiates charging of high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al., and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 27 under the control of control circuitry 79 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above-cited patent issued to Mehra and in U.S. Pat. No. 4,727,877 to Kallok, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads. As used herein, IMD 10 encompasses all implantable medical devices of any kind that receive electrical signals from heart 8.

Electrical signals from heart 8 may be used to monitor blood insulin and/or blood glucose levels. In particular, there is a relationship between insulin-mediated uptake of glucose and cardiac monophasic action potential. By monitoring cardiac electrical activity, therefore, insulin-mediated uptake of glucose may also be monitored.

Figure 6:
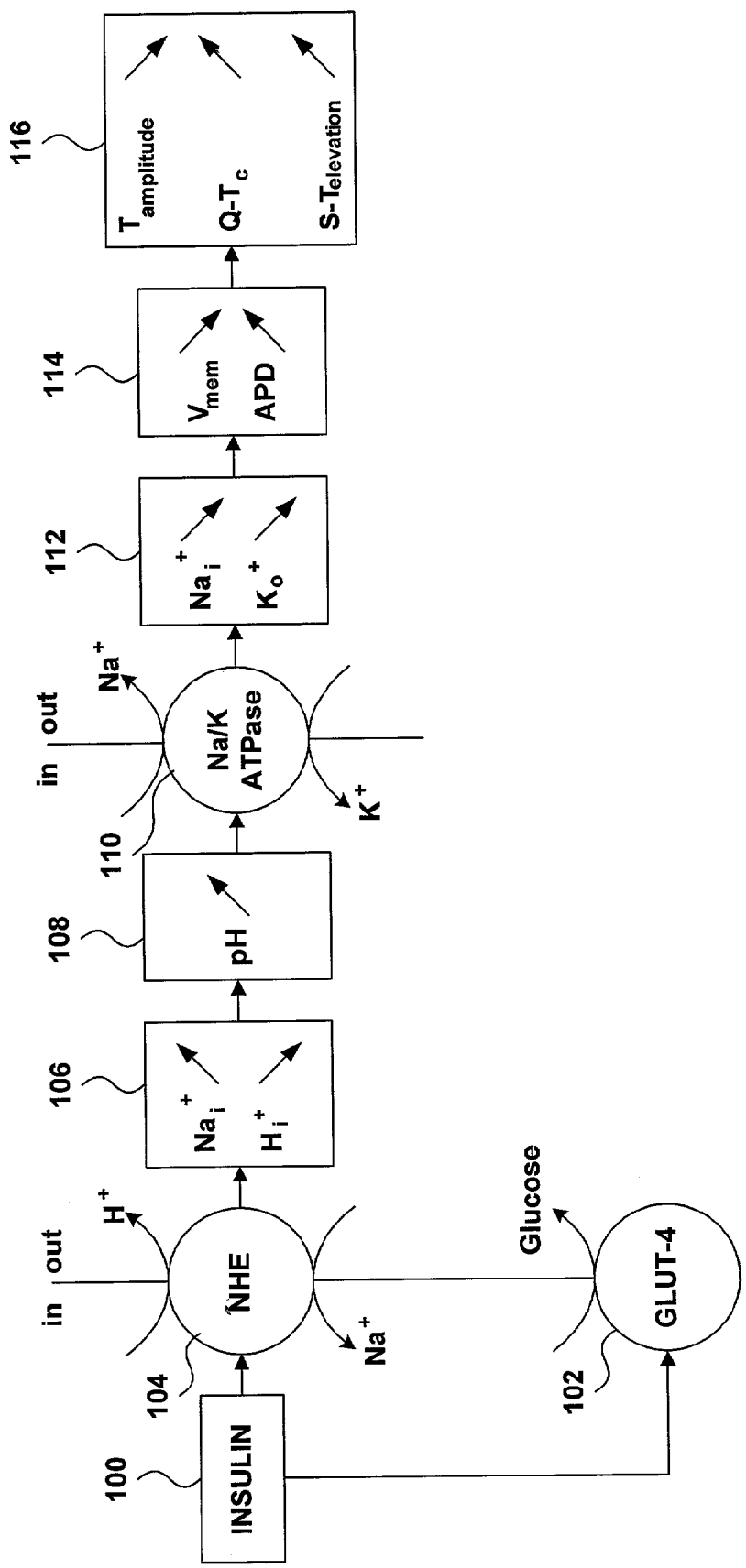
FIG. 6 is a process diagram that illustrates the physiological relationship between insulin-mediated uptake of glucose and cardiac electrical signals.

FIG. 6 illustrates a manner in which insulin-mediated uptake of glucose affects cardiac electrical signals. Insulin 100 may be secreted in response to an elevated blood glucose level, which often occurs after ingestion of a meal. Insulin 100 may be secreted by the pancreas or by an implanted insulin delivery device. Insulin 100 facilitates glucose transport into most cells. In particular, a glucose transporter such as GLUT-4 102 helps transport glucose across the cell membrane in response to insulin 100. Insulin 100 further triggers other processes not shown in FIG. 6, such as stimulation of glycogenesis, inhibition of glycogenolysis, inhibition of gluconeogenesis, and conversion of ADP to ATP.

In cardiac muscle cells, insulin 100 acts upon the sodium-hydrogen exchanger 104, causing sodium ions to enter the cell and hydrogen ions to leave the cell. As a result, sodium ion concentration inside the cell ($Na_i^+$) increases and hydrogen ion concentration inside the cell ($H_i^+$) decreases (106). Because of the intracellular loss of hydrogen ion, pH inside the cell increases (108).

The increase in pH (108) has an effect upon the sodium-potassium pump 110, also called the $Na^+$—$K^+$ ATPase pump. Sodium ions are pumped out of the cell and potassium ions are pumped into the cell. As a result, the concentration of sodium ions inside the cell ($Na_i^+$) declines and the concentration of potassium ions outside the cell ($K_o^+$) declines as well (112). The change in ion concentrations on opposite sides of the cell membrane causes the resting membrane potential ($V_{mem}$) to become more negative due to hyperpolarization (114). Because the resting membrane potential is negative, hyperpolarization results in an increase in the absolute value of the resting membrane potential. The change in ion concentrations also causes the action potential duration (APD) to increase (114).

In cardiac muscle cells, the APD increase affects the T-wave amplitude in an ECG or an EGM. In particular, the APD increase causes the T-wave amplitude to decrease (116). In particular, the T-wave amplitude decreases in comparison to the amplitude of the R-wave, which may be used as a reference. The T-wave is the electrical signal that accompanies repolarization of the ventricular cardiac muscle.

The APD increase also has an affect on the Q-T interval. In particular, the APD increases the Q-T interval, i.e., the time between the Q-wave, which accompanies the onset of ventricular depolarization, and the T-wave (116). The Q-T interval may be corrected for the RR interval and may be abbreviated Q-$T_c$.

Furthermore, the change in membrane potential may be observed as an S-T elevation (116). Between the S-wave, which accompanies the end of ventricular depolarization, and the T-wave, which accompanies ventricular repolarization, the electrical signal generated by the heart should be approximately zero volts. The change in membrane potential, however, may manifest itself as an elevated potential between the S-wave and the T-wave.

The effects of insulin-mediated glucose uptake shown in FIG. 6 apply to muscle cells throughout the body. These effects in cardiac muscle cells, however, result in artifacts that may be detected by an implanted device that receives an EGM signal from heart 8. The EGM signal reflects insulin-mediated glucose uptake, and the implanted device can monitor insulin-mediated glucose uptake by monitoring and analyzing the EGM signal. In particular, the implanted device can monitor changes in insulin-mediated glucose uptake by monitoring and analyzing changes in the EGM signal.

Figure 7:
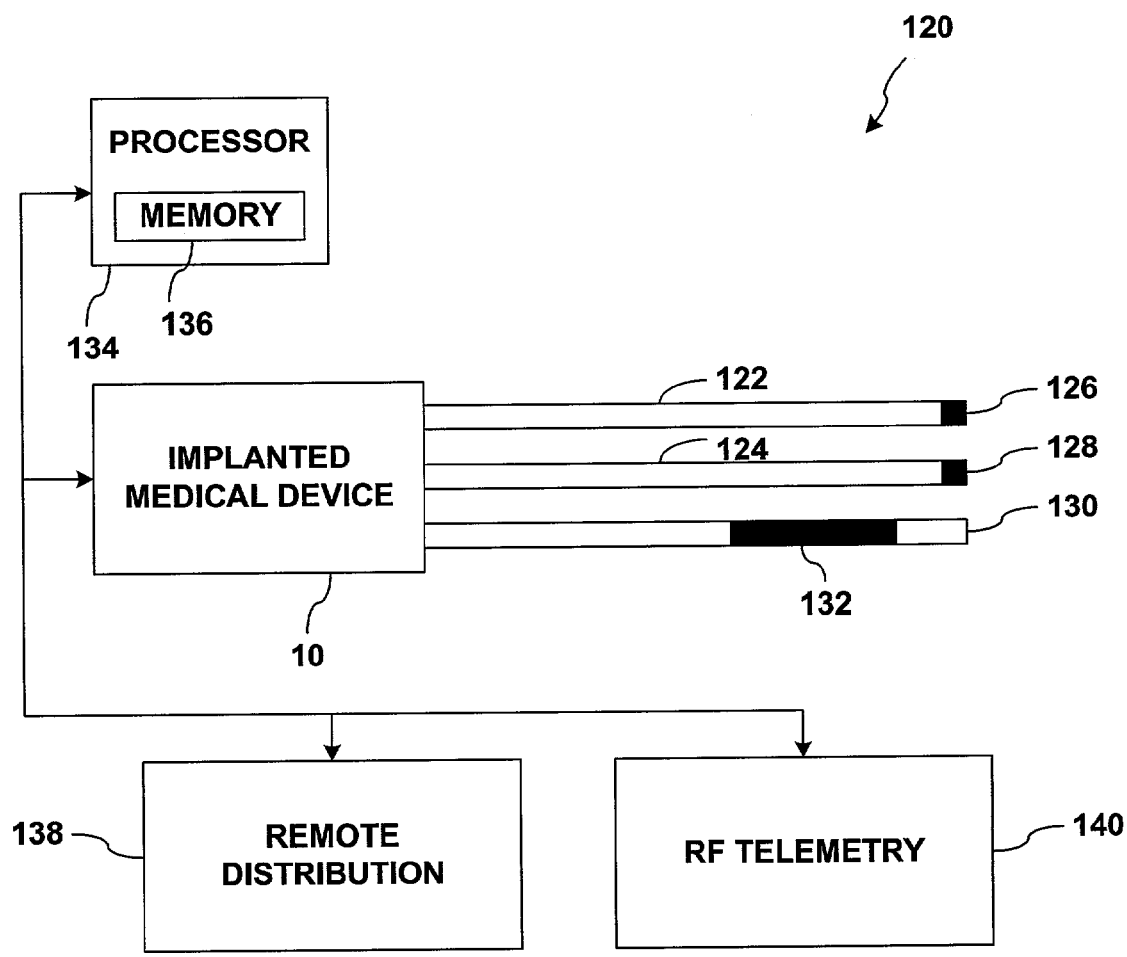
FIG. 7 is a diagram of a system including an implantable medical device.

FIG. 7 shows a system 120 illustrating an embodiment of the invention, in which EGM signals are used to monitor insulin-mediated glucose uptake. System 120, which may be implantable in a human being or a mammal, includes IMD 10. IMD 10 may be a pacemaker or a pacemaker-cardioverter-defibrillator as illustrated in FIGS. 1–5, but IMD 10 may also be any medical device that receives electrical signals from heart 8. IMD 10 may be, for example, an implantable pressure monitor, an implantable nerve stimulator, an implantable muscle stimulator, an implantable drug delivery device or an implantable monitoring device such as a cardiac monitoring device.

In many cases, IMD 10 may have a principal function other than monitoring insulin-mediated glucose uptake or monitoring the progress of IGT or diabetes. The principal function may be to monitor a signal other than a heart signal, or to diagnose a condition other than insulin-mediated glucose uptake. The principal function may also be a therapeutic function other than delivery of insulin, such as delivery of electrical stimulation or pharmaceutical substances. IMD 10 may have any combination of principal monitoring, diagnostic and/or therapeutic functions.

A pressure monitor, in one example, may monitor blood pressures in one or more chambers of heart 8 via one or more pressure sensors that supply pressure signals to the pressure monitor. In addition to monitoring blood pressures, the pressure monitor may perform diagnostic functions such as estimating cardiac output. A pacemaker, in another example, may monitor heart signals, identify and classify cardiac rhythms, and may delivery therapy to heart 8 in response to certain detected arrhythmias. In devices such as a pressure monitor and a pacemaker, insulin-mediated glucose uptake monitoring may be performed in addition to the other functions. In other words, insulin-mediated glucose uptake monitoring may be "piggy-backed" onto an IMD 10 that may another principal function. A patient may receive a pacemaker because of heart problems, for example, and the pacemaker monitors the patient's EGM for arrhythmias. The same pacemaker may also provide insulin-mediated glucose uptake monitoring as an additional benefit. In these cases, the patient need not have been diagnosed with IGT or diabetes.

When insulin-mediated glucose uptake monitoring is "piggy-backed" onto an IMD, the monitoring may be performed using the pre-existing hardware of the IMD. In particular, the IMD may include hardware, such as sensing electrodes, for receiving cardiac signals. By processing the cardiac signals received via the hardware, the IMD may monitor insulin-mediated glucose uptake without needing significant additional sensing hardware.

In some embodiments of the invention, however, the invention may be a stand-alone device. In other words, the invention may be embodied as an implantable monitoring device that has the principal function of monitoring the progress of IGT or diabetes. Such a device may be provided to a patient who, although not diagnosed with IGT or diabetes, is at risk of developing the disease. Such a device may be provided to a patient who has been diagnosed with IGT or diabetes, and who wishes to monitor the efficacy of treatment.

IMD 10 may receive electrical signals from heart 8 via one or more electrodes disposed upon one or more leads. FIG. 7 shows system 120 with leads, such as leads 122 and 124, with electrodes 126 and 128 disposed thereon. The invention is not limited to two electrodes and two leads, but encompasses any number of electrodes. Moreover, multiple electrodes may be disposed upon a single lead, and it is not necessary to the invention that each electrode have a dedicated lead. When IMD 10 is a pacemaker, electrodes 126 and 128 may serve as sensing and pacing electrodes.

The invention is not limited to any particular electrode placement. When IMD 10 is a pacemaker, for example, electrodes 126, 128 may be placed in or proximate to one or more chambers of heart 8. Electrodes 126, 128 need not be placed in or proximate to heart 8, however, but may be placed such that electrodes 126, 128 can detect the electrical signals of heart 8. In general, the closer electrodes 126, 128 are to heart 8, the more pronounced the signals of interest may be, which may facilitate processing the signals.

IMD 10 may also be coupled to leads, sensors or devices that do not sense the electrical activity of heart 8. When IMD 10 is a pacemaker-cardioverter-defibrillator, for example, system 10 may include a lead 130 that couples IMD 10 to a defibrillation coil electrode 132. Defibrillation coil electrode 132 need not have a dedicated lead 130, but may be coupled to another lead such as lead 122 or lead 124. When IMD 10 is another kind of device, IMD 10 may be coupled to other leads, sensors and/or stimulators, such as a pressure sensor, an activity sensor, a muscle stimulator or a temperature sensor (not shown in FIG. 7).

IMD 10 may be coupled to a processor 134. Processor 134 is associated with memory 136. Memory 136 may store data such as measured parameters related to insulin-mediated glucose uptake. Processor 134 is shown as logically separate from IMD 10, but in practice processor 134 may be housed inside IMD 10, and IMD 10 and processor 134 may be realized as a single implantable device. Processor 134 and memory 136 may be included in microprocessor 51 and random access memory 59 in the embodiment of IMD 10 shown in FIG. 5, for example. Alternatively, processor 134 or memory 136 may be physically separate from IMD 10.

Processor 134 analyzes electrical signals from heart 8 sensed by electrodes 126, 128 and received by IMD 10. Processor 134 may, for example, perform digital signal analysis on the electrical signals. The digital signal analysis may include making measurements of R-wave amplitude, T-wave amplitude and Q-T interval, and monitoring for S-T elevation. Data collected in this way may be stored in memory 136.

Data collected by processor 134 may be retrieved via input/output devices such as remote distribution link 138 or RF telemetry 140. Further, processor 134 may receive information such as data or programming via input/output devices 138, 140. Remote distribution link 138 may provide a channel for uploading or downloading information over a telephone line or over the internet, for example. RF telemetry 140 may communicate information on a dedicated wireless channel. Typically, a patient is required to visit an office of a physician when information is to be uploaded or downloaded via RF telemetry 140.

Figure 8:
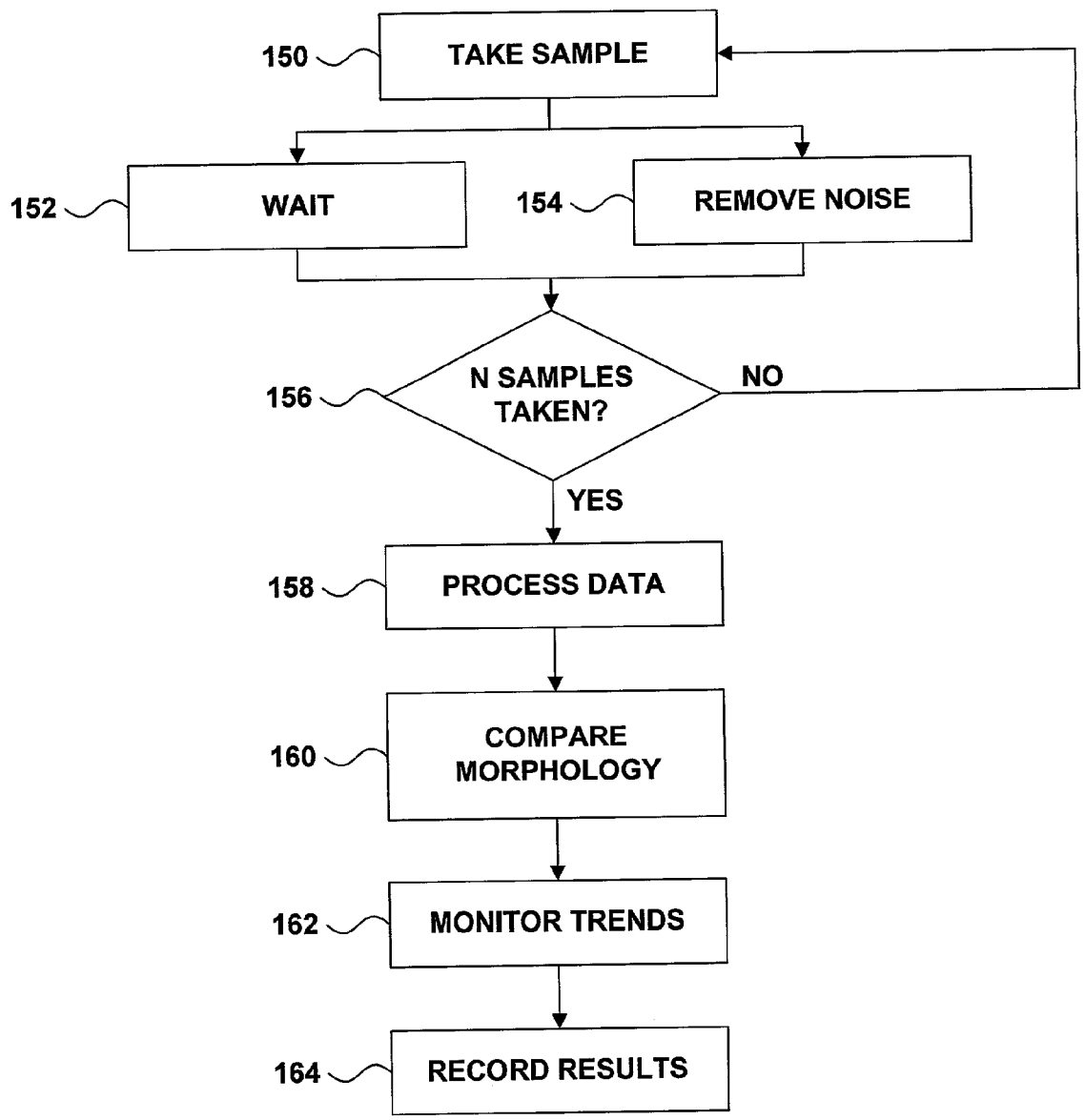
FIG. 8 is a flow diagram showing techniques for collecting and processing data pertaining to the monitoring of blood insulin and/or blood glucose.

FIG. 8 illustrates exemplary techniques that may be applied by system 120 for monitoring blood insulin and/or blood glucose. In a typical embodiment, processor 134 is responsible for the monitoring. Processor 134 may, for example, regulate data collection, perform signal analysis and perform computations as needed.

The monitoring techniques may be applied on a regular basis, such as every week or every other week. Typically, a patient's progression toward diabetes is sufficiently gradual that monitoring need not be performed on an hour-to-hour or day-to-day basis. The invention may be applied with any monitoring frequency, however, which may be programmed into processor 134 by the patient's physician. Because system 120 may be powered by a battery such as battery power source 76 shown in FIG. 3, less frequent monitoring may conserve battery life.

Monitoring may be triggered by an ingestion of a meal. Monitoring may be triggered automatically by a sensor that detects a meal, for example, or may be triggered by the patient using a device such as input/output device 138, 140. In a healthy patient, insulin-mediated glucose uptake activity rises from a starting level following a meal. As ingested nutrients are absorbed and enter the blood stream, insulin levels rise to promote cellular uptake of glucose and conversion of carbohydrates into glycogen. Within 30 to 50 minutes after a meal, insulin-mediated glucose uptake activity typically reaches a peak in a healthy patient. Insulin-mediated glucose uptake activity thereafter declines. After about two hours, insulin-mediated glucose uptake activity returns approximately to its starting level. Total absorption of a typical meal takes about four hours.

In a patient with IGT, which is often a precursor to Type II diabetes, insulin-mediated glucose uptake activity following a meal may be morphologically different from the insulin-mediated glucose uptake activity in a healthy patient. In particular, insulin-mediated glucose uptake activity may reach a peak more slowly, may peak at a far lower level than in a healthy patient, and may decline more gradually.

In a patient having Type II diabetes, these differences are more pronounced. Following a meal, insulin-mediated glucose uptake activity peaks at a far lower value than that exhibited by a healthy patient and may not peak for more than an hour after the meal. Instead of showing a marked rise and decline of insulin-mediated glucose uptake activity, a diabetic patient exhibits comparatively little change in insulin-mediated glucose uptake activity following a meal. The absence of marked change in insulin-mediated glucose uptake is due to the cell's reduced sensitivity to insulin.

Because insulin-mediated glucose uptake is reflected in the EGM, analysis of the EGM signal may indicate whether the patient may have IGT or diabetes. In a healthy patient, EGM parameters such as T-wave amplitude, Q-T interval and S-T elevation change following ingestion of a meal, as insulin-mediated glucose uptake takes place. A patient having IGT may show changes in the EGM parameters to a lesser degree, and a patient having diabetes may show few changes in EGM parameters after a meal.

To monitor insulin-mediated glucose uptake, therefore, processor 134 takes a sample of ECG data (150). The monitoring may begin after a meal. The first sample may be taken immediately after the meal or following a waiting period. Sampling (150) may last for about a minute, for example. During one minute of sampling, a typical heart beats about sixty times or more, so each sample includes signals from several cardiac cycles. Processor 134 may then wait in an idle mode (152) for a period of time, such as nine minutes, before taking another sample. Samples may be collected over a time period such as two hours.

While in idle mode, processor 134 may assume a low-power configuration, thereby conserving battery power. Processor 134 may also perform some signal processing while waiting. Processor 134 may, for example, remove the noise from the sample (154) using any of several analog and/or digital techniques. One exemplary technique for removing noise is to average the signals from the several cardiac cycles, generating an average electrical signal for a single cardiac cycle. The sampled signal may be separated into a plurality of cardiac cycle signals, using the R-wave as a reference that separates one cardiac cycle signal from another. The average signal may be generated by summing the individual cardiac cycle signals and dividing by the number of cardiac cycles in the sample. Alternatively, individual cardiac signals may be summed and/or averaged on a beat-to-beat basis during sampling (150).

Another noise reduction technique may include rejection of atypical data. Whether the data are atypical or not may be detected by several techniques. If system 120 includes a pacemaker, for example, system 120 may include logic or algorithms for recognizing and classifying various types of arrhythmia. Sensors such as pH sensors or temperature sensors may also be employed to identify atypical data or eliminate artifacts from the data.

After the waiting period (152) expires, processor 134 may take another sample (150). The number of samples, N, may be varied as desired. When N samples have been taken (156), the sampled data may be processed (158). By performing digital signal analysis on each set of sampled data, and by analyzing parameters such as R-wave and T-wave amplitudes, Q-T interval and S-T elevation, processor 134 can determine the insulin-mediated glucose uptake activity that followed the meal, and how the activity varied over time.

The most recent insulin-mediated glucose uptake activity may then be compared to previous insulin-mediated glucose uptake activity, or to a reference insulin-mediated glucose uptake activity, or both (160). Morphological analysis may include techniques such as performing a simple difference calculation, applying a correlation function, comparing frequency components or using any of a number of statistical tools.

Processor 134 may also monitor the data for trends (162). Processor 134 may compare the most recent insulin-mediated glucose uptake activity to prior insulin-mediated glucose uptake activity, which may have a bearing upon whether the patient is progressing to diabetes.

Another trend-monitoring technique is to compare the most recent insulin-mediated glucose uptake activity to a reference activity. The reference activity may be, for example, the insulin-mediated glucose uptake activity monitored under controlled conditions. The farther the most activity departs from the reference, the greater the likelihood that the patient is progressing toward diabetes.

An additional trend-monitoring technique may be to combine the data pertaining to the most recent samplings with data collected previously by, for example, exponential averaging. Processor 134 may also perform any of several statistical analyses, such as calculation of variance parameters, computation of mean and standard deviation, or computation of maximum minus minimum values. Further, processor 134 may apply techniques such as artificial neural network techniques or fuzzy interferencing or the application of genetic algorithms. The invention is not limited to these trend-monitoring techniques, and any or all of them may be employed. The results of processing, comparing and trend-monitoring may be recorded in memory 136 (164).

There are many variations to the techniques shown in FIG. 8, and the invention encompasses all of the variations. For example, some data processing (158) may be performed following the taking of each sample (150), rather than after the taking of all of the samples. The sampling interval may be longer or shorter than a minute, and the waiting period (152) may be shorter or longer than nine minutes. Samples may be taken over a time frame that is shorter or longer than two hours.

In some circumstances, the processed sampled data may indicate that the patient's condition is very serious. In such cases, processor 134 may initiate a patient alert. A patient alert may include, for example, generation of an audible alarm that informs the patient to see his physician right away.

In many cases, however, the processed sampled data will remain stored in memory 136 until the patient's next scheduled appointment with his physician. During the appointment, the physician may interrogate system 120 via input/output devices 138, 140. The data may be organized in any useful form, and the physician may use the data to determine whether the patient is at risk of developing diabetes. The physician may, for example, order blood tests for diabetes when the data indicates that the patient's insulin-mediated glucose uptake activity is anomalous.

The invention may offer several advantages. One advantage is that patients having an implantable device such as a pacemaker, a pacemaker-cardioverter-defibrillator, an implantable pressure monitor, an implantable nerve stimulator, an implantable muscle stimulator, an implantable drug delivery device or an implantable monitoring device may receive blood insulin and/or blood glucose monitoring with the implantable device. There is no need to implant a separate, dedicated insulin or glucose monitoring device. Moreover, in some embodiments, the implanted device can be configured to provide blood insulin and/or blood glucose monitoring without substantial structural modifications.

In addition, the invention uses electrical sensors that are long-lasting and are often functional under a wide variety of conditions. Chemical-based glucose sensors or insulin sensors may not be as robust as electrical sensors.

Moreover, the techniques of the invention help identify problems that may not be otherwise identified. Type II diabetes develops slowly and usually progresses unnoticed by the patient. The techniques of the invention allow the long-term progress of the condition to be monitored and brought to the attention of the patient and his physician. With warning of the development of IGT or Type II diabetes, the patient and the physician can take preventive steps, apply appropriate treatment, and avoid development of serious complications. So far, there is no cure for diabetes, but treatment such as administration of oral glucose lowering agents, proper diet and exercise and can slow, and even reverse, the progression of the disease. The patient may have more therapeutic options available when the disease is detected early.

The preceding specific embodiments are illustrative of the practice of the invention. It is to be understood, therefore, that other expedients known to those skilled in the art or disclosed herein may be employed without departing from the invention or the scope of the claims. For example, many of the embodiments described above are directed to monitoring insulin-mediated glucose uptake activity for diagnostic purposes. The invention is not limited to diagnostic functions, however. The invention may also include additional diagnostic and/or therapeutic functions. Additional diagnostic functions may include, for example, initiation of further glucose metabolic experiments. Therapeutic functions may include, for example, delivery of medication following analysis of the sampled data.

Although the invention may be applied to track the potential development of diabetes, the invention is not limited to that application. When the patient becomes aware of the development of IGT or Type II diabetes, the patient and the physician may take steps to address the condition. The invention may be applied to monitor the effectiveness of the steps, especially over a long term. The invention includes within its scope all applications of blood glucose or blood insulin monitoring.

The invention further includes within its scope the methods of making and using the systems described above. These methods are not limited to the specific examples described above, but may be adapted to meet the needs of a particular patient. The invention also includes within its scope any of computer-readable media comprising instructions for causing a programmable processor, such as microprocessor, to carry out the techniques described above. Such computer-readable media include, but are not limited to, magnetic and optical storage media. Such computer-readable media may be accessed by an external programmer, for example. Computer-readable media also includes read-only memory such as. erasable programmable read-only memory or flash memory that may be accessed by the implanted processor. These and other embodiments are within the scope of the following claims.

In the claims, means-plus-functions clauses are intended to cover the recited structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

The invention claimed is:

1. An implantable medical device system comprising:
an implantable medical device that receives an electrical signal from a heart, wherein the implantable medical device comprises at least one of a pacemaker, a pacemaker-cardioverter-defibrillator, an implantable pressure monitor, an implantable nerve stimulator, an implantable muscle stimulator, an implantable drug delivery device, and an implantable cardiac monitor; and
a processor coupled to the implantable medical device that monitors insulin-mediated glucose uptake as a function of the electrical signal,
wherein the implantable medical device receives a signal in addition to the electrical signal from the heart.

2. The system of claim 1,
wherein the processor monitors insulin-mediated glucose uptake by monitoring at least one of a T-wave amplitude in the electrical signal, a Q-T interval in the electrical signal and an S-T elevation in the electrical signal.

3. The system of claim 1, further comprising memory coupled to the processor.

4. The system of claim 1, wherein the implantable medical device and the processor are included in a single implantable device.

5. The system of claim 1, further comprising an electrode coupled to the implantable medical device, wherein the implantable medical device receives the electrical signal from the electrode.

6. The system of claim 5, wherein the electrode is disposed in a chamber of the heart.

7. The system of claim 1, wherein the implantable medical device monitors a condition in addition to insulin-mediated glucose uptake.

8. The system of claim 1,
wherein the implantable medical device delivers a therapy other than delivery of insulin.

9. The system of claim 1, wherein the implantable medical device analyzes at least one of a heart rhythm and a pressure in the heart.

10. The system of claim 1,
wherein the implantable medical device delivers at least one of pacing pulses, defibrillation, nerve stimulation and muscle stimulation.

11. An implantable medical device system comprising:
an implantable medical device that receives an electrical signal from a heart, wherein the implantable medical device comprises at least one of a pacemaker, a pacemaker-cardioverter-defibrillator, an implantable pressure monitor, an implantable nerve stimulator, an implantable muscle stimulator, an implantable drug delivery device, and an implantable cardiac monitor; and
a processor coupled to the implantable medical device that monitors insulin-mediated glucose uptake as a function of the electrical signal, wherein the implantable medical device receives an activity signal from an activity sensor, a pressure signal from a pressure sensor and a temperature signal from a temperature sensor.

12. A medical device system comprising:

a medical device that receives an electrical signal from a heart, wherein the medical device includes at least one of a pacemaker, a pacemaker-cardioverter-defibrillator, a pressure monitor, a nerve stimulator, a muscle stimulator, a drug delivery device, a monitor, and a cardiac monitor; and a processor coupled to the medical device that monitors insulin-mediated glucose uptake as a function of the electrical signal, wherein the medical device receives a signal in addition to the electrical signal from the heart.

13. The system of claim 12, wherein the processor monitors insulin-mediated glucose uptake by monitoring at least one of a T-wave amplitude in the electrical signal, a Q-T interval in the electrical signal and an S-T elevation in the electrical signal.

14. The system of claim 12, further comprising memory coupled to the processor.

15. The system of claim 12, wherein the medical device and the processor are included in a single device.

16. The system of claim 12, further comprising an electrode coupled to the medical device, wherein the medical device receives the electrical signal from the electrode.

17. The system of claim 16, wherein the electrode is disposed in a chamber of the heart.

18. The system of claim 12, wherein the medical device monitors a condition in addition to insulin-mediated glucose uptake.

19. The system of claim 12, wherein the medical device delivers a therapy other than delivery of insulin.

20. The system of claim 12, wherein the medical device delivers at least one of pacing pulses, defibrillation, nerve stimulation and muscle stimulation.

21. A medical device system comprising:

a medical device that receives an electrical signal from a heart, wherein the medical device includes at least one of a pacemaker, a pacemaker-cardioverter-defibrillator, a pressure monitor, a nerve stimulator, a muscle stimulator, a drug delivery device, a monitor, and a cardiac monitor; and a processor coupled to the medical device that monitors insulin-mediated glucose uptake as a function of the electrical signal, wherein the medical device receives an activity signal from an activity sensor, a pressure signal from a pressure sensor and a temperature signal from a temperature sensor.

22. A medical device system comprising:

a medical device that receives an electrical signal from a heart, wherein the medical device includes at least one of a pacemaker, a pacemaker-cardioverter-defibrillator, a pressure monitor, a nerve stimulator, a muscle stimulator, a drug delivery device, a monitor, and a cardiac monitor; and a processor coupled to the medical device that monitors insulin-mediated glucose uptake as a function of the electrical signal, wherein the medical device analyzes at least one of a heart rhythm and a pressure in the heart.

* * * * *